(12) United States Patent
Hovde

(10) Patent No.: US 6,611,335 B1
(45) Date of Patent: Aug. 26, 2003

(54) TONE BURST DIODE LASER SPECTROSCOPY

(75) Inventor: David Christian Hovde, Cincinnati, OH (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 09/640,804

(22) Filed: Aug. 17, 2000

Related U.S. Application Data

(60) Provisional application No. 60/149,504, filed on Aug. 17, 1999.

(51) Int. Cl.[7] .............................................. G01N 21/61
(52) U.S. Cl. ....................................................... 356/437
(58) Field of Search ......................................... 356/437

(56) References Cited

U.S. PATENT DOCUMENTS

| | | |
|---|---|---|
| 3,568,047 A | 3/1971 | Look et al. |
| 4,297,035 A | 10/1981 | Bjorklund |
| 4,765,736 A | 8/1988 | Gallagher et al. |

OTHER PUBLICATIONS

Adams, H., et al., "Sensitivity Improvement of Tone–burst Modulated Spectroscopy with a Color–Center Laser," *J. Opt. Soc. Am. B*, vol. 1, No. 5, pp 710–714 (Oct. 1984).

Chan, M–C., et al., "Laser spectroscopic Studies of the Pure Rotational $U_0(0)$ and $W_0(0)$ Transitions of Solid Parahydrogen," *J. Chem Phys.*, vol. 95, No. 1, pp 88–97 (Jul. 1991).

Goldstein, N., et al., "Measurement of Molecular Concentrations and Line Parameters Using Line–Locked Second Harmonic Spectroscopy with an AlGaAs Diode Laser," *Applied Optics*, vol. 31, No. 18, pp 3409–3415 (Jun. 20, 1992).

Gudeman, C.S., et al., "Tone–Burst Modulated Color–Center–Laser Spectroscopy," *Optics Letters*, vol. 8, No. 6, pp 310–312 (Jun. 1983).

Iguchi, T., "Modulation Waveforms for Second–Harmonic Detection with Tunable Diode Lasers," *J. Opt. Soc., Am B*, vol. 3, No. 3, pp 419–425 (Mar. 1986).

Kluczynski, P., et al., "Theoretical Description Based on Fourier Analysis of Wavelength–Modulation Spectrometry in Terms of Analytical and Background Signals," *Applied Optics*, vol. 38, No. 27, pp 5803–5815 (Sep. 20, 1999).

Pavone, F.S., et al., "Frequency– and Wavelength–Modulation Spectroscopies: Comparison of Experimental Methods Using an AlGaAs Diode Laser," *Applied Physics B*, vol. 56, pp 118–122 (1993).

(List continued on next page.)

*Primary Examiner*—Richard A. Rosenberger
(74) *Attorney, Agent, or Firm*—Jeffrey D. Myers

(57) ABSTRACT

A tone burst spectrometer and spectrometry method comprising employing a narrow bandwidth light source, a tone burst modulation waveform generator, synchronization of a lock-in amplifier to a burst frequency of the generator, and one or more of the following: use of a semiconductor laser; setting the tone frequency of the generator to an integer multiple of the burst frequency; using a tone modulation waveform other than a sine wave; setting the tone frequency of the generator to less than a half width at half maximum of a targeted spectral transition; and producing a spectral feature with a high signal to noise ratio while synchronizing the lock-in amplifier to the tone frequency of the generator or an odd harmonic of the tone frequency and wherein the output of the lock-in amplifier is low pass filtered and negative feedback is employed to stabilize the operating wavelength at or near a center wavelength of a spectral feature of the sample.

18 Claims, 3 Drawing Sheets

OTHER PUBLICATIONS

Pickett, H.M., "Determination of Collisional Linewidths and Shifts by a Convolution Method," *Applied Optics*, vol. 1, No. 16, ppp 2745–2749 (Aug. 15, 1980).

Sasada H., et al., "Ti–Sapphire Laser Spectrometer for Doppler–Limited Molecular Spectroscopy," *J. Opt. Soc. Am. B.*, vol. 11, No. 1, pp 191–197 (Jan. 1994).

Silver, J.A., "Frequency–Modulation Spectroscopy for Trace Species Detection: Theory and Comparison Among Experimental Methods," *Applied Optics*, vol. 31, No. 6, pp 707–717 (Feb. 20, 1992).

Cassidy, D.T., et al., "Harmonic Detection with Tunable Diode Lasers—Two–Tone Modulation," *Apl. Phys*, B 29, pp 279–285 (1982).

TONE BURST DIODE LASER SPECTROSCOPY

CROSS-REFERENCE TO RELATED APPLICATIONS

This application claims the benefit of the filing of U.S. Provisional Patent Application Ser. No. 60/149,504, entitled Tone Burst Spectroscopy Method for Diode Laser Spectroscopy, filed on Aug. 17, 1999, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. NAS2-14367 awarded by the U.S. National Aeronautics and Space Administration and Contract No. 68-D-99-069 awarded by the U.S. Environmental Protection Agency.

BACKGROUND OF THE INVENTION

1. Field of the Invention (Technical Field)

The present invention relates to tone burst spectroscopy and to diode laser spectroscopy.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Absorption spectrometry is a widely used method for measuring the presence or concentration of chemical compounds. Modulation techniques have been widely used to improve the sensitivity of absorption spectrometers. In these techniques, the optical frequency or wavelength of a light source is rapidly varied, and the output of the spectrometer is analyzed in a way that exploits the wavelength dependence of the compound under study. Modulation techniques improve sensitivity, in part because the lasers that are used as light sources typically have less noise at high frequencies. Such noise typically follows a 1/f distribution, where f is the frequency. In addition to tone burst spectroscopy, modulation techniques include wavelength modulation, frequency modulation, and two-tone frequency modulation. These other modulation techniques have been described in many publications, for example Pavone et al., "Frequency- and wavelength-modulation spectroscopies: comparison of experimental methods using an AlGaAs diode laser," *Applied Physics* B, 56, 118–122 (1993); J. A. Silver, "Frequency Modulation Spectroscopy for Trace Species Detection: Theory and Comparison Among Experimental Methods," *Applied Optics* 31, 707–717 (1991); P. Kluczynski et al., "Theoretical description based on Fourier analysis of wavelength-modulation spectrometry in terms of analytical and background signals," *Applied Optics* 38, 5803–5815 (September 1999); G. Bjorklund, *Method and Device for Detecting a Specific Spectral Feature*, U.S. Pat. No. 4,297,035 (1981); and T. Gallagher et al., *Frequency Modulation Spectroscopy Using Dual Frequency Modulation and Detection*, U.S. Pat. No. 4,765,736 (1988). Frequency modulation and wavelength modulation methods effectively avoid laser 1/f noise, but they introduce strong amplitude modulation of the laser at the modulation frequency. This amplitude modulation can be 10% of the laser power and may differ from the detection frequency by a factor of two, making it difficult to remove by filtering. Two tone modulation avoids both laser 1/f noise and amplitude modulation at frequencies near the detection frequency, but at a cost of a lower theoretical signal to noise ratio.

In the tone burst method, the light from the laser (or other narrow band source) is transmitted through a sample and on to a detector that produces an electrical output proportional to the transmitted power. The laser's optical frequency or wavelength is modulated at a tone frequency F1 and the modulation is turned on and off at some lower, burst frequency F2. The output of the photodetector, suitably amplified, is measured with a lock-in amplifier referenced to the frequency F2. The output of the lock-in is a measure of the difference in transmission with and without the modulation. A strong signal is produced when the laser wavelength is near the wavelength of a narrow spectral transition. Detection at F2 avoids laser excess noise at still lower frequencies. Tone burst spectroscopy thus provides a practical method for sensitive detection of small, wavelength dependent absorbances.

Tone burst spectroscopy is effective because the tone modulation spreads the laser output across a range of wavelengths that is wider than the absorption feature being examined. If the average (i.e., unmodulated) laser wavelength is nearly coincident with the center of an absorption feature then more light is transmitted through the sample when the tone modulation is on than when the tone modulation is off. In other words, when the tone modulation is on, some of the laser output is shifted away from the center of the absorption feature to the wings of the absorption feature where the absorption is weaker. Switching the tone modulation on and off at the burst frequency produces a synchronous change in the amount of light that is transmitted through the sample to the detector. Thus, the detector output also changes synchronously with the burst modulation and the extent of change is a measure of the optical absorbance.

Tone burst spectroscopy has been developed by a number of workers. H. M. Pickett, "Determination of collisional linewidths and shifts by a convolution method," *Applied Optics* 19, 2745–2749 (1980), first applied the tone burst method to absorption spectroscopy in microwave experlements. C. S. Gudeman et al., "Tone-burst Modulated Color-center-laser Spectroscopy," *Optics Letters*, Vol. 8. pp. 310–312 (1983). demonstrated the use of lone burst spectroscopy with a color center laser. To modulate the frequency of the laser, an electro-optic modulator was used. The tone burst modulation waveform was generated from two oscillators, the F1 oscillator operating at 400 MHz and the F2 oscillator at 10–100 kHz. these oscillators were combined in a radio frequency mixer, amplified, and used to drive the electro-optic modulator crystal. Problems that arose included reflections within the optical system and overheating of the modulator. H. Adams et al., "Sensitivity Improvement of Tone-burst Modulated Spectroscopy with a Color-center Laser," *J. Opt. Soc. Amer.* B (1984) Vol. 1, No. 5, pp. 710–714, improved the tone burst method with a specially designed electro-optic modulator which was wedged to reduce the effects of reflections and water cooled to prevent overheating. The tone frequency (200–300 MHz) was generated by an rf generator, while the burst frequency was generated using a separate square wave generator at 10–100 kHz.

M. C. Chan et al., "Laser Spectroscopic Studies of the Pure Rotational U0(0) and W0(0) Transitions of Solid Parahydrogen," *J. Chem. Phys.* Vol. 95, No. 1, pp. 88–97 (1991), demonstrated the use of tone burst detection on solid samples. The tone frequency was 40 MHz, the burst frequency was 6 kHz, and the two oscillators used to produce these frequencies were coupled using a double-balanced mixer.

H. Sassada et al., "Ti-Sapphire Laser Spectrometer for Doppler-limited Molecular-Spectroscopy," *J. Opt. Soc. Amer.* B Vol. 11, pp. 191–197 (1994), notes the close connection between tone burst spectroscopy and two-tone frequency modulation spectroscopy. Two oscillators are used, the tone at 196 MHz and the burst at 930 kHz. The burst oscillator is used to drive an RF switch. The switched output is amplified and coupled to an electro-optic modulator.

In implementing tone burst detection, there are some constraints on the frequencies of the tone (F1) and the burst (F2). Previous work has used tone frequencies F1 that are comparable to or greater than the line width of the spectral transition to be measured. This corresponds to the frequency modulation regime in frequency modulation spectroscopy (see Silver). The modulation bandwidth of the light source sets a practical upper limit on the modulation frequency, which may make it difficult to measure broad transitions using tone burst in the frequency modulation limit. The burst frequency F2 must be less than half the tone frequency F1 and must be within the bandwidth of the detector and lock-in amplifier. Typically, the burst frequency is a small fraction of the tone frequency, e.g., the burst frequency was approximately $1/200$ the tone frequency in the work by Sassada.

In the studies cited above, the tone frequency F1 was much greater than the burst frequency F2. As a result, any amplitude modulation of the laser at the tone frequency is easily suppressed by the filters associated with the detection circuitry. However, the use of higher modulation frequencies demands a higher degree of care in designing electrical circuitry to generate and control the modulation. Changes in reactance can change the modulation amplitude, altering the calibration of the spectrometer. Thus it may be desirable to employ a lower value for the tone frequency. When the tone frequency is close to the burst frequency, amplitude modulation at the tone frequency may cause an unwanted signal at the burst frequency. The magnitude and phase of this interfering signal will depend on the exact frequency and phase relationship of the tone and burst frequencies. If these frequencies are generated independently from separate oscillators, then the phase and amplitude of the interference may drift due to variations in the frequencies of these oscillators.

Lock-in amplifiers or phase sensitive detectors are used to recover the signal at the burst frequency. These have a signal input and a reference input that defines the measurement frequency. The reference input usually is converted to a calibrated amplitude, but it can have an adjustable phase. The lock-in amplifier signal input for tone burst is the output of the photodetector after any preampliers, and the reference input is the burst frequency F2. The lock-in amplifier output is usually a voltage or a digitized value that indicates the amplitude of the signal at the frequency F2. There are many different circuit implementations of a lock-in, including double balanced mixers, switched capacitor filters, transistor multiplier circuits and digital signal processors that take the product of the digitized input signal times a reference waveform. These implementations vary in cost, sensitivity, size, power consumption, and other features that may affect the selection for a particular application. However, it is important to distinguish between two classes of lock-in amplifiers based on their function. The "True sine wave" lock-in has an output that is proportional only to the sinusoidal part of the input signal at the reference frequency. Mathematically, the output is proportional to the signal input times a sine wave at the reference frequency. The "square wave" lock-in has an output that is proportional to the signal input times a symmetrical square wave at the reference frequency (N. Goldstein et al., "Measurement of molecular concentrations and line parameters using line-locked second harmonic spectroscopy with an AlGaAs diode laser," *Applied Optics* 31, 3409–3415 (1992). In either the square wave or sine wave lock-in, the output depends further on the reference phase angle. It is also possible to measure the signal amplitude at the frequency F2 by phase-less techniques such as can be provided by a quadrature phase lock-in or by suitable filters and an ac voltmeter.

D. C. Look et al., Apparatus and Method for Measuring Nuclear Spin-lattice Relaxation Time (T1) by Tone-burst Modulation, U.S. Pat. No. 3,568,047, describe the use of tone burst modulation in nuclear magnetic resonance spectroscopy. A magnetic field modulation, either sinusoidal or triangular, is applied to the sample using of a coil. The frequency ratio of the tone relative to the burst is controlled, so that the burst contains a precise number of tone periods with a constant phase. The tone burst is also used to synchronize an oscilloscope, and an oscillogram of the magnetization induced in the sample is recorded and analyzed to determine the spin-lattice relation time.

The present invention provides a means to stabilize the phase relationship between the tone and burst frequencies so that the effects of amplitude modulation at the tone frequency are constant in time. It further provides a method to reduce the interference by choosing the number of modulation periods contained within the burst. These improvements permit the use of lower tone frequencies or higher burst frequencies without compromising the sensitivity of the measurement. The invention further provides for a variety of tone modulation waveforms.

SUMMARY OF THE INVENTION
(DISCLOSURE OF THE INVENTION)

The present invention is of a tone burst spectrometer and spectrometry method comprising: providing a semiconductor laser with an input controlling operating wavelength and a light output; passing the light through an area containing a sample; detecting the light with a detector; generating a tone burst modulation waveform via a generator connected to the wavelength control input of the semiconductor laser; and synchronizing a lock-in amplifier connected to an output of the detector to a burst frequency of the generator.

The present invention is also of a tone burst spectrometer and spectrometry method comprising: providing a narrow bandwidth light source with an input controlling operating wavelength and a light output; passing the light through an area containing a sample; detecting the light with a detector; generating a tone burst modulation waveform via a generator connected to the wavelength control input of the semiconductor laser; and synchronizing a lock-in amplifier connected to an output of the detector to a burst frequency of the generator; and wherein the tone frequency of the generator is an integer multiple of the burst frequency. In the preferred embodiment, the tone frequency is either an odd integer multiple of the burst frequency and the lock-in amplifier is a "sine wave" type lock-in amplifier, or a multiple of four times the burst frequency and the lock-in amplifier is a "square wave" type lock-in amplifier.

The present invention is further of a tone burst spectrometer and spectrometry method comprising: providing a narrow bandwidth light source with an input controlling operating wavelength and a light output; passing the light through an area containing a sample; detecting the light with a detector; generating a tone burst modulation waveform via a generator connected to the wavelength control input of the semiconductor laser; and synchronizing a lock-in amplifier connected to an output of the detector to a burst frequency of the generator; and wherein the tone modulation waveform is other than a sine wave. In the preferred embodiment, the tone modulation waveforms a square wave or a triangle wave. The tone modulation waveform preferably comprises a filtered noise waveform produced by high pass filtering a white noise source to remove noise components at the burst frequency and lower frequencies.

The present invention is additionally of a tone burst spectrometer and spectrometry method comprising: providing a narrow bandwidth light source with an input controlling operating wavelength and a light output; passing the light through an area containing a sample; detecting the light with a detector; generating a tone burst modulation waveform via a generator connected to the wavelength control input of the semiconductor laser; and synchronizing a lock-in amplifier connected to an output of the detector to a burst frequency of the generator; and wherein the tone frequency of the generator is less than a half width at half maximum of a targeted spectral transition.

The present invention is also of a tone burst spectrometer and spectrometry method comprising: providing a narrow bandwidth light source with an input controlling operating wavelength and a light output; passing the light through an area containing a sample in sufficient concentration to produce a spectral feature with a high signal to noise ratio; detecting the light with a detector; generating a tone burst modulation waveform via a generator connected to the wavelength control input of the light source; and synchronizing a lock-in amplifier connected to an output of the detector to a tone frequency of the generator or an odd harmonic of the tone frequency; and wherein the output of the lock-in amplifier is low pass filtered and negative feedback is employed to stabilize the operating wavelength at or near a center wavelength of a spectral feature of the sample.

A primary object of the present invention is to stabilize the phase relationship between the tone and burst frequencies so that the effects of amplitude modulation at the tone frequency are constant in time.

Another object of the invention is to reduce interference by choosing the number of modulation periods contained within a tone burst.

A primary advantage of the present invention is that it permits the use of lower tone frequencies or higher burst frequencies without compromising the sensitivity of the measurement.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED
EMBODIMENTS (BEST MODES FOR
CARRYING OUT THE INVENTION)

The advantages of the present invention can be obtained with any spectrometer that can be rapidly wavelength modulated with a modulation depth comparable to the characteristic line width of the spectral feature to be detected. A detailed description of the tone burst spectroscopy of the invention as applied to tunable diode laser spectroscopy illustrates the invention.

Figure 1:
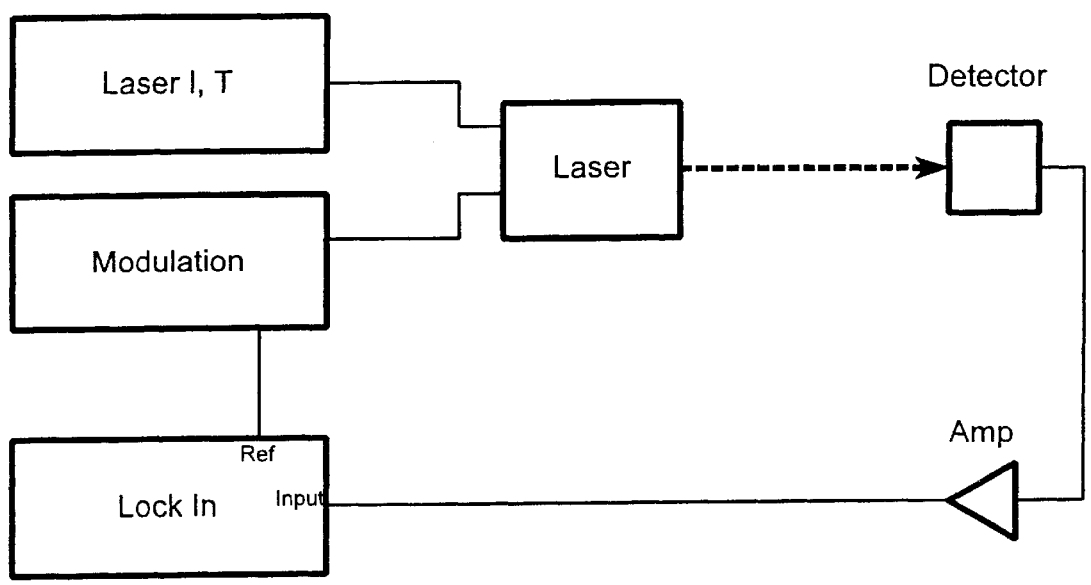
FIG. 1 is a schematic diagram of the tone burst apparatus of the present invention; the laser passes through a gas sample or the atmosphere to a detector, the resulting photo current is amplified and detected with a lock in amplifier referenced to the low frequency F2; the modulation waveform preferably applied to the laser is shown in FIG. 2.

An apparatus for performing tunable diode laser tone burst measurements according to the invention, shown in FIG. 1, preferably comprises a diode laser with a suitable collimating lens, temperature control electronics for stabilizing the diode laser temperature, current control electronics, current modulation electronics, a gas sample region, a detector and amplifier, and a lock-in detection circuit. The lock-in detection circuit can be interfaced to a computer for displaying spectra or it can be connected to an indicator that shows the strength of the signal at the detection frequency F2.

For purposes of the specification and claims, "lock-in detection" and "lock-in amplifier" refers to any technique or device that can measure amplitude at a particular frequency, including phase-less techniques.

Semiconductor lasers, such as InGaAsP diode lasers and vertical cavity surface emitting (VCSEL) lasers of the type used for communications, or AlGaAs diode lasers used in compact disk players, can be operated by injecting current directly into the laser. The injection current can be modulated, providing a simple method for wavelength modulation of the laser, since the wavelength is a function of the injection current. However, the light power is also usually a function of injection current. Usually the light output is nearly a linear function of current above some threshold current. When current modulation is used to modulate the wavelength of a tunable semiconductor laser, an advantage of tone burst spectroscopy over wavelength modulation or frequency modulation spectroscopy is that the power modulation that accompanies current modulation is centered on the high frequency F1. When F1 is much greater than F2, it is very easy to build a filter to separate the power modulation from the desired signal. Compared to two-tone fm spectroscopy, tone burst is simpler to implement, is more flexible, and has larger theoretical signal to noise ratio.

Laser amplitude modulation can induce an unwanted tone burst signal, particularly when the tone frequency is not much larger than the burst frequency. This signal may be out of phase with the spectral signal, yet difficulties in precisely determining the demodulation phase angle can result in some contamination of the tone burst signal by the laser amplitude modulation signal. When the tone frequency F1 is an exact integer multiple of the burst frequency F2, then a definite phase relationship will exist between the two frequencies and there will be a well-defined number of tone modulation cycles during each burst. As a result, any effects of laser amplitude modulation will be constant from burst to burst. This uniformity is difficult to accomplish using separate oscillators, which can drift independently. For instance, the oscillators used by Sasada at 196 MHz and 930 kHz bear a ratio of about 211:1. For the phase relationship to be stable over a period of just one second, these oscillators would need to maintain their frequencies to within 1 Hz, or about one part in 200,000,000 for the tone frequency. For a practical measurement device that must remain calibrated over weeks or even months, the relative oscillator frequency stability requirement is still more stringent.

Achieving and maintaining an integer ratio of the tone frequency to the burst frequency is much simpler when the two frequencies are generated from a single oscillator. This can be done using an oscillator to generate the tone frequency and digital counters to generate the burst frequency, or by using a phase-locked loop to generate the tone frequency from an oscillator at the burst frequency, and combining the waveforms as described by Gudemann or by Sasada. Alternatively, the desired tone burst waveform can be produced by a digital waveform synthesizer using values computed for appropriately sequenced intervals, for example using an SRS DS340 (Stanford Research Systems, Palo Alto, Calif.). When using this commercial device, a particularly convenient method involves computing the tone values for one burst at 8192 points and downloading these values to the digital signal generator, taking care that the last value corresponds to a voltage of zero. It is important that the tone frequency is below the Nyquist sampling frequency, so that there should be fewer than 4096 cycles of the tone in the burst. Then an external oscillator is used to trigger the digital waveform synthesizer and also to reference the lock-in amplifier. The digital waveform synthesizer is set to put out a single burst of the tone frequency when triggered. The time base of the oscillator and the clock rate of the digital frequency synthesizer are adjusted to give an approximately 50% duty cycle for the tone.

When the tone frequency F1 is a sine wave at an odd harmonic of the burst frequency F2, that is, F1=n×F2 where n=3, 5, 7 and the burst waveform has a 50% duty cycle, a half-integer number of periods is contained in the burst. If the lock-in amplifier is sensitive only to the sine wave component at the burst frequency (a "true sine wave" lock-in such as the model SR 830 DSP lock-in from Stanford Research Systems), then no signal is detected by the lock-in due to linear amplitude modulation of the light source, regardless of the lock-in detection phase. This simplifies the measurement of weak absorption signals and permits the use of phaseless demodulation techniques with reduced background.

When the tone frequency F1 is a multiple of four times the burst frequency F2, that is, F1=n×F2, where n=4, 8, 12 . . . , and the burst waveform has a 50% duty cycle, an even integer number of periods is contained in each burst. If the lock-in amplifier is a square wave demodulator, such as a switched capacitor filter with a wide input bandwidth of many times the burst frequency, then no signal is detected by the lock-in due to linear amplitude modulation of the light source, regardless of the lock-in detection phase. This simplifies the measurement of weak absorption signals and permits the use of phaseless demodulation techniques with reduced background.

As noted by Sasada, a close connection exists between tone burst spectroscopy and two-tone spectroscopy. Two-tone can be viewed as a special case of tone burst spectroscopy. However, tone burst is a much more general technique. For instance, the tone waveform could be a sine wave, a square wave, or a triangle wave. Just as with wavelength modulation spectroscopy, Iguchi, "Modulation waveforms for second-harmonic detection with tunable diode lasers," *J. Optical Society America* B, 3, 419–423 (1986), different waveforms are more or less susceptible to noise or to interference fringes. The tone waveform can even be a noise waveform, high-pass filtered to remove components at or below the burst frequency.

In particular, based on the results of Iguchi and the theory of tone burst spectroscopy, a triangle tone waveform is expected to be much less sensitive to the presence of most etalon fringes than the usual sine wave. Likewise, a square wave tone waveform is expected to be much less sensitive to white noise. Choice of the waveform can be made based on the factors that limit the sensitivity of the measurement.

Previous implementations of tone burst spectroscopy have used a high tone frequency that is comparable to the line width of the transition being studied. This approach works well for narrow spectral features. However, for pressure broadened lines in gases, or to detect broad, unresolved spectral features from polyatomic molecules, the line width may be in the range of 1 GHz or higher. Many lasers can not be modulated at such high frequencies. Others can be modulated at these frequencies, but the coupling circuitry is prone to drift due to changes in reactance. As a result, the tone modulation amplitude could change in time, which would result in a change in sensitivity to spectral features.

However, tone burst can be used equally well with modulation frequencies much less than the line width of the transition being detected, provided that the modulation depth is sufficiently large. Good sensitivity can be maintained with a low modulation frequency when the product of the modulation frequency and the number of sidebands with significant power is of the order of the transition line width expressed in frequency units. This corresponds to the wavelength modulation limit in wavelength modulation spectroscopy (see Silver).

For many applications it is desirable to stablilize the average light wavelength at the center of the absorption feature. Standard line locking techniques use negative feedback of an error signal to some input of the laser that controls its wavelength. In the case of a diode laser, the feedback adjusts its injection current or junction temperature. When the gain is adjusted appropriately, the long-term deviations from the target wavelength can be kept quite small.

The tone burst technique does not permit a direct measure of the error signal. However, the error signal can be determined by lock-in detection at the tone wavelength F1 or one of its odd harmonics. The concentration of the absorber should be sufficient to produce a large signal to noise ratio. The output of the lock-in amplifier should be smoothed with a low pass filter for which the cut-off frequency is much lower than the burst frequency F2. The lock-in signal monitors wavelength drift of the laser in much the same way that a wavelength modulation line-locking system monitors wavelength drift. However, the lower duty cycle results in a smaller signal to noise ratio than in the wavelength modulation case. Usually this in not a problem as the smaller signal to noise ratio can be made up for with a higher concentration or path length of the absorber species.

Industrial Applicability

The invention is further illustrated by the following non-limiting examples.

EXAMPLE 1

Figure 2:
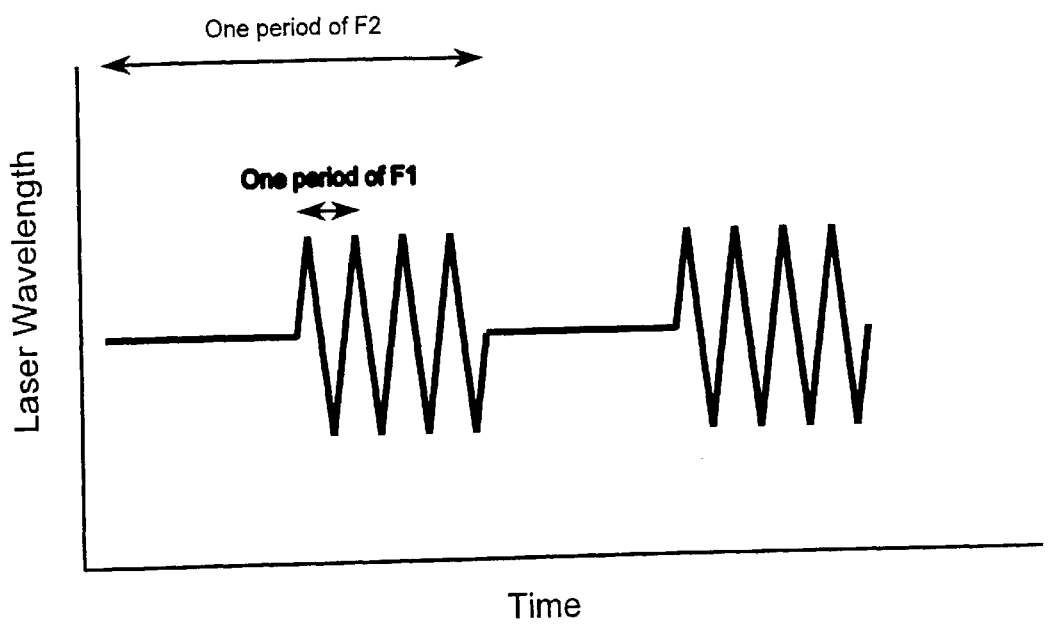
FIG. 2 illustrates the tone burst waveform of the present invention; the high frequency, F1, turns on and off at a period given by the burst frequency, F2.
Figure 3:
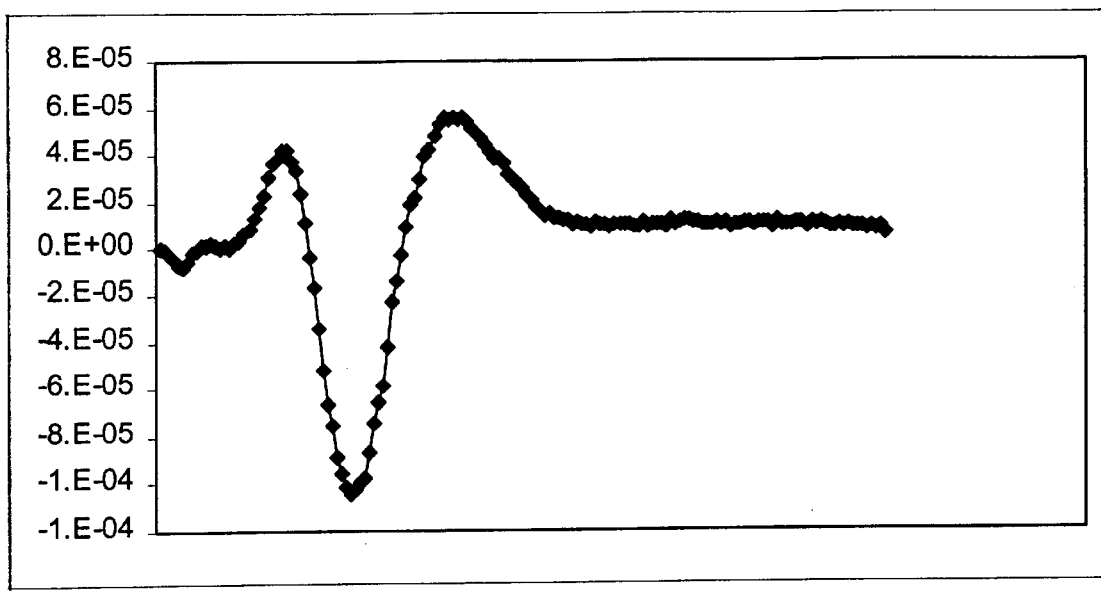
FIG. 3 illustrates the tone burst modulation spectrum of methane near 1650 nm; the spectrum is approximately the second derivative of the transmission line shape; the spectrum is obtained by ramping the current of the diode laser while modulating with a tone burst waveform, demodulating the output of a photodetector with a lock-in amplifier referenced to the burst frequency.

In a test of the tone burst method, a commercially available, 1650 nm, distributed feedback diode laser (#14046, Anritsu, Japan), a form of InGaAsP semiconductor laser, was mounted on a copper block whose temperature was stabilized by means of a thermoelectric cooler and a thermistor interfaced to an ILX LDC 3722 diode laser controller. The laser current was also controlled by the diode laser controller. A ball lens, anti-reflection coated in the near infrared, was positioned in front of the laser to collimate the output. An InGaAs photodiode (ETX 1000T, Epitaxx, N.J.) was positioned to receive the light and the amplified detector output was applied to the signal input of a lock-in amplifier. The modulation waveform was generated from a clock at F1 using standard TTL circuit components. Two synchronous 8 bit counters and a flip flop generated F2 from F1. The two waveforms at F1 and F2 were combined using a logical AND followed by a high pass filter with the cut-off frequency set above F2 to produce a waveform similar to that shown in FIG. 2. There were 256 periods of the high frequency modulation F1 in very ON half-cycle of the burst frequency F2. A sample of methane diluted in nitrogen was placed in he optical path to give an absorption signal of about 0.1%. The output of the lock-in amplifier was monitored as a function of the dc laser injection current. Ramping the dc current swept the laser wavelength through the methane absorption line near 1650 nm. The lock-in was referenced to F2 and the output was a large signal to noise waveform with a second derivative line shape. Numerical simulations also produce this second derivative line shape.

EXAMPLE 2

Figure 4:
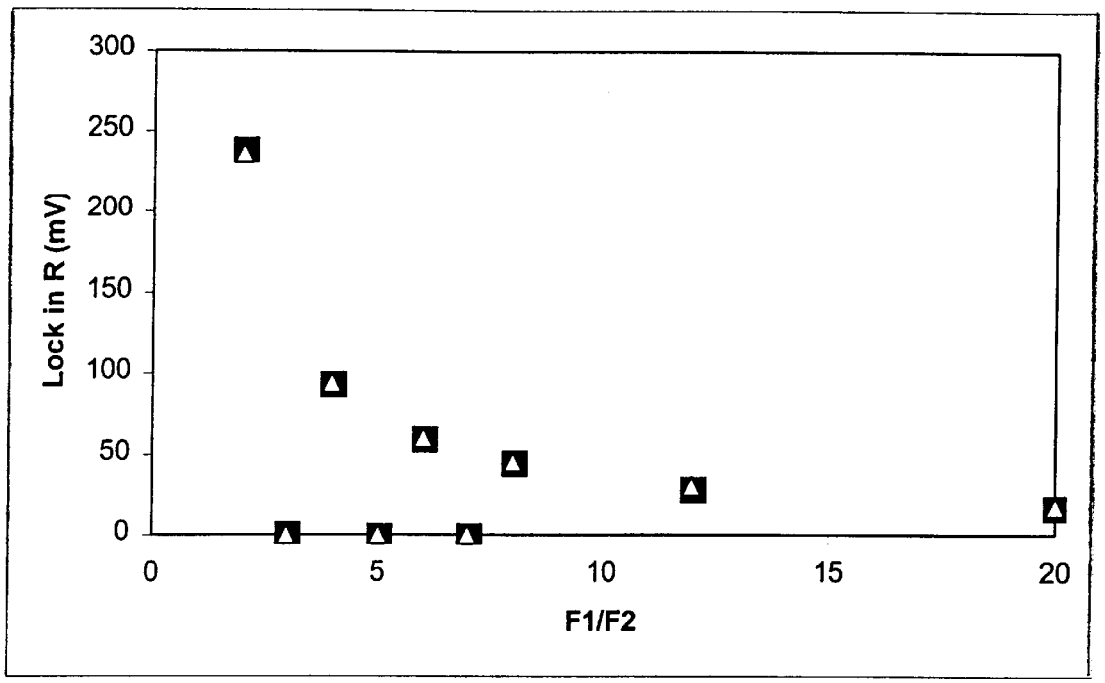
FIG. 4 illustrates the results of using different periods in the modulation according to the invention, namely the results of an investigation of the effect of amplitude modulation on tone burst spectroscopy as a function of the ratio of the tone frequency F1 to the burst frequency F2; the solid squares show experimental data; the unfilled triangles are the values expected from a numerical mode, scaled to agree with the data at F1/F2=4.

A second test involved modulating the Anritsu laser with a sinusoidal tone waveform produced by a digital waveform generator and demodulating the photodetector signal using a sine wave lock-in. The waveform generator was adjusted to produce approximately 50% duty factor bursts. The frequency ratio F1/F2 was varied and the lock-in output offset, produced as a result of laser amplitude modulation, was recorded. The results are shown in FIG. 4 as the square symbols. A numerical simulation of the tone burst modulation and lock-in demodulation was performed for the same conditions, shown as the unfilled triangle symbols. The results of the simulation were scaled to the experimental results at one tone period per burst. Theory and experiment are in excellent agreement. In particular, for F1/F2 an odd integer, both theory and experiment show negligible offset from laser amplitude modulation.

EXAMPLE 3

A third test involved simulations of a sinusoidal tone waveform with square wave demodulation. As in the previous example, the lock-in offset was studied as a function of the frequency ratio F1/F2. For F1/F2 an integer multiple of four, the offset was zero.

The preceding examples can be repeated with similar success by substituting the generically or specifically described reactants and/or operating conditions of this invention for those used in the preceding examples. In particular, while the examples given have been the detection of a gas by tone burst spectroscopy using tunable diode lasers, other samples can be detected as well, such as liquids or solids.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A tone burst spectrometer comprising:
   a semiconductor laser with operating wavelength controlled by laser injection current modulation;
   an area containing a sample through which the light passes;
   a detector;
   a tone burst modulation waveform generator connected to said wavelength control input of said semiconductor laser; and
   a lock-in amplifier synchronized to a burst frequency of said generator and connected to an output of said detector.

2. A tone burst spectrometer comprising:
   a narrow bandwidth light source with an input controlling operating wavelength and a light output;
   an area containing a sample through which the light passes;
   a detector;
   a tone burst modulation waveform generator connected to said wavelength control input of said light source; and
   a lock-in amplifier synchronized to a burst frequency of said generator and connected to an output of said detector; and
   wherein a tone frequency of said generator is an integer multiple of said burst frequency.

3. The spectrometer of claim 2, wherein said tone frequency is an odd integer multiple of said burst frequency and said lock-in amplifier comprises a "sine wave" type lock-in amplifier.

4. The spectrometer of claim 2, wherein said tone frequency is a multiple of four times said burst frequency and said lock-in amplifier comprises a "square wave" type lock-in amplifier.

5. A tone burst spectrometer comprising:
   a narrow bandwidth light source with an input controlling operating wavelength and a light output;
   an area containing a sample through which the light passes;
   a detector;
   a tone burst modulation waveform generator connected to said wavelength control input of said light source; and
   a lock-in amplifier synchronized to a burst frequency of said generator and connected to an output of said detector; and
   wherein a tone modulation waveform of said generator is other than a sine wave.

6. The spectrometer of claim 5 wherein said tone modulation waveform is selected from the group consisting of square waves and triangle waves.

7. The spectrometer of claim 5 wherein said tone modulation waveform comprises a filtered noise waveform produced by high pass filtering a white noise source to remove noise components at the burst frequency and lower frequencies.

8. A tone burst spectrometer comprising:
 a narrow bandwidth light source with an input controlling operating wavelength and a light output;
 an area containing a sample in sufficient concentration to produce a spectral feature with a high signal to noise ratio through which the light passes;
 a detector;
 a tone burst modulation waveform generator connected to said wavelength control input of said light source; and
 a lock-in amplifier synchronized to a tone frequency of said generator or an odd harmonic of said tone frequency and connected to an output of said detector; and
 wherein an output of said lock-in amplifier is used with low pass filtering means and negative feedback means to stabilize said operating wavelength at or near a center wavelength of a spectral feature of the sample.

9. A tone burst spectrometry method comprising the steps of;
 providing a semiconductor laser with operating wavelength controlled by laser injection current modulation;
 passing the light through an area containing a sample;
 detecting the light with a detector;
 generating a tone burst modulation waveform via a generator connected to the wavelength control input of the semiconductor laser; and
 synchronizing a lock-in amplifier connected to an output of the detector to a burst frequency of the generator.

10. A tone burst spectrometry method comprising the steps of:
 providing a narrow bandwidth light source with an input controlling operating wavelength and a light output;
 passing the light through an area containing a sample;
 detecting the light with a detector;
 generating a tone burst modulation waveform via a generator connected to the wavelength control input of the semiconductor laser; and
 synchronizing a lock-in amplifier connected to an output of the detector to a burst frequency of the generator; and
 wherein in the generating step a tone frequency of the generator is an integer multiple of the burst frequency.

11. The method of claim 10, wherein in the generating step the tone frequency is an odd integer multiple of the burst frequency and the lock-in amplifier comprises a "sine wave" type lock-in amplifier.

12. The method of claim 10, wherein in the generating step the tone frequency is a multiple of four times the burst frequency and the lock-in amplifier comprises a "square wave" type lock-in amplifier.

13. A tone burst spectrometry method comprising the steps of:
 providing a narrow bandwidth light source with an input controlling operating wavelength and a light output;
 passing the light through an area containing a sample;
 detecting the light with a detector;
 generating a tone burst modulation waveform via a generator connected to the wavelength control input of the semiconductor laser; and
 synchronizing a lock-in amplifier connected to an output of the detector to a burst frequency of the generator; and
 wherein in the generating step the tone modulation waveform is other than a sine wave.

14. The method of claim 13, wherein in the generating step the tone modulation waveform is selected from the group consisting of square waves and triangle waves.

15. The method of claim 13, wherein in the generating step the tone modulation waveform comprises a filtered noise waveform produced by high pass filtering a white noise source to remove noise components at the burst frequency and lower frequencies.

16. A tone burst spectrometry method comprising the steps of:
 providing a narrow bandwidth light source with an input controlling operating wavelength and a light output;
 passing the light through an area containing a sample in sufficient concentration to produce a spectral feature with a high signal to noise ratio;
 detecting the light with a detector;
 generating a tone burst modulation waveform via a generator connected to the wavelength control input of the light source; and
 synchronizing a lock-in amplifier connected to an output of the detector to a tone frequency of the generator or an odd harmonic of the tone frequency; and
 wherein in the synchronizing step an output of the lock-in amplifier is low pass filtered and negative feedback is employed to stabilize the operating wavelength at or near a center wavelength of a spectral feature of the sample.

17. A tone burst spectrometer comprising:
 a semiconductor laser with an input controlling operating wavelength and a light output;
 an area containing a sample through which the light passes;
 a detector;
 a tone burst modulation waveform generator connected to said wavelength control input of said semiconductor laser; and
 a lock-in amplifier synchronized to a burst frequency of said generator and connected to an output of said detector; and
 wherein said tone modulation waveform comprises a filtered noise waveform produced by high pass filtering a white noise source to remove noise components at the burst frequency and lower frequencies.

18. A tone burst spectrometry method comprising the steps of:
 providing a narrow bandwidth light source with an input controlling operating wavelength and a light output;
 passing the light through an area containing a sample;
 detecting the light with a detector;
 generating a tone burst modulation waveform via a generator connected to the wavelength control input of the semiconductor laser; and
 synchronizing a lock-in amplifier connected to an output of the detector to a burst frequency of the generator; and
 wherein in the generating step the tone modulation waveform is other than a sine wave; and
 wherein in the generating step the tone modulation waveform comprises a filtered noise waveform produced by high pass filtering a white noise source to remove noise components at the burst frequency and lower frequencies.

* * * * *